(12) United States Patent
Minami et al.

(10) Patent No.: US 11,071,288 B2
(45) Date of Patent: Jul. 27, 2021

(54) AQUACULTURE SHRIMPS AND METHODS FOR CULTURING SAME

(71) Applicant: NIPPON SUISAN KAISHA, LTD., Tokyo (JP)

(72) Inventors: Hiroshi Minami, Saiki (JP); Kosuke Matsuoka, Saiki (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 187 days.

(21) Appl. No.: 16/277,763

(22) Filed: Feb. 15, 2019

(65) Prior Publication Data

US 2019/0216059 A1      Jul. 18, 2019

Related U.S. Application Data

(63) Continuation of application No. PCT/JP2017/029474, filed on Aug. 16, 2017.

(30) Foreign Application Priority Data

Aug. 16, 2016   (JP) .............................. JP2016-159512

(51) Int. Cl.

| | | |
|---|---|---|
| *A01K 61/59* | (2017.01) | |
| *A61K 35/612* | (2015.01) | |
| *A23K 20/105* | (2016.01) | |
| *A23K 50/80* | (2016.01) | |
| *A23L 17/40* | (2016.01) | |
| *A23K 20/179* | (2016.01) | |
| *A61P 43/00* | (2006.01) | |

(52) U.S. Cl.
CPC ............ *A01K 61/59* (2017.01); *A23K 20/105* (2016.05); *A23K 20/179* (2016.05); *A23K 50/80* (2016.05); *A23L 17/40* (2016.08); *A61K 35/612* (2013.01); *A61P 43/00* (2018.01); *Y02A 40/81* (2018.01)

(58) Field of Classification Search
CPC ...... A01K 61/59; A23K 20/179; A23K 50/80; A23K 20/105; A23L 17/40; A61P 43/00; A61K 35/612
See application file for complete search history.

(56) References Cited

U.S. PATENT DOCUMENTS

| | | | |
|---|---|---|---|
| 2006/0130162 A1 | 6/2006 | Kyle et al. | |
| 2006/0265766 A1* | 11/2006 | Kyle | A23K 20/179 800/13 |
| 2011/0092726 A1* | 4/2011 | Clarke | C01C 1/04 554/175 |

FOREIGN PATENT DOCUMENTS

| | | |
|---|---|---|
| JP | 4-53455 A | 2/1992 |
| JP | 6-276956 A | 10/1994 |
| JP | 7-170886 | 7/1995 |
| JP | 2006-508651 | 3/2006 |

OTHER PUBLICATIONS

International Search Report dated Nov. 14, 2017, in Application No. PCT/JP2017/029474.

(Continued)

*Primary Examiner* — Monica L Barlow
*Assistant Examiner* — Aaron M Rodziwicz
(74) *Attorney, Agent, or Firm* — Oblon, McClelland, Maier & Neustadt, L.L.P.

(57) ABSTRACT

An aquacultured shrimp contains carotenoid and does not have a broken 2nd antenna.

24 Claims, 4 Drawing Sheets

(56) References Cited

OTHER PUBLICATIONS

Extended European Search Report dated Mar. 18, 2020, in Patent Application No. 17841534.5, 8 pages.
Zhang, J. et al., "Effects of dietary astaxanthin on growth, antioxidant capacity and gene expression in Pacific white shrimp *Litopenaeus vannamei*", Aquaculture Nutrition, XP055672676, vol. 19, No. 6, Dec. 1, 2013, pp. 917-927.
Negre-Sadargues G et al: "utilization of synthetic carotenoids by the prawn *Penaeus japonicus* reared under laboratory Conditions", Aquaculture, XP008047729, vol. 110, No. 2, Jan. 1, 1993, pp. 151-159.
Niti Chuchird et al: "Effect of dietary formic acid and astaxanthin on the survival and growth of Pacific white shrimp (*Litopenaeus vannamei*) and their resistance to Vibrio parahaemolyticus", Springerplus, XP055672578, vol. 4, No. 1, Aug. 21, 2015, 12 pages.
Ana Cristina Diaz et al: "Effect of Dietary Astaxanthin on Free Radical Scavenging Capacity and Nitrite Stress Tolerance of Postlarvae Shrimp, *Pleoticus muelleri*", Journal of Agricultural and Food Chemistry, XP055672683, vol. 62, No. 51, Dec. 24, 2014, pp. 12326-12331.

\* cited by examiner

AQUACULTURE SHRIMPS AND METHODS FOR CULTURING SAME

CROSS-REFERENCE TO RELATED APPLICATIONS

The present application is a continuation of International Application No. PCT/JP2017/029474, filed Aug. 16, 2017, which is based upon and claims the benefits of priority to Japanese Application No. 2016-159512, filed Aug. 16, 2016. The entire contents of these applications are incorporated herein by reference.

BACKGROUND OF THE INVENTION

Field of the Invention

The present specification relates to aquaculture shrimps and applied products utilizing the same as well as a method used in the aquaculturing the shrimps.

Discussion of the Background

One of the problems exhibited by shrimps grown in an aquaculture system is the occurrence of so-called blue shrimps where the body color of the shrimp turns into blue.

Carotenoids (for example, astaxanthin) are involved in the body color of shrimps, and it is known that the major cause of the occurrence of blue shrimp is due to an insufficient carotenoid content in the body.

Carotenoids are either obtained directly from feed or metabolically converted from other carotenoids contained in feed.

For this reason, feed used in the culturing of shrimps (shrimp feed) is supplemented with carotenoids such as astaxanthin (for example, Patent Documents 1 and 2).
Patent Document 1: JP H4-53455 A
Patent Document 2: JP H6-276956 A

SUMMARY OF THE INVENTION

According to an aspect of the present invention, an aquaculture shrimp includes a carotenoid, and second antenna which is not broken.

According to another aspect of the present invention, an aquaculture shrimp has value a of body color 2 days after killing in ice with water, which is greater than or equal to −1.26.

According to yet another aspect of the present invention, a method of rearing an aquaculture shrimp includes rearing by land-farming which includes giving feed including greater than or equal to 50 ppm of astaxanthin.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings. Though embodiments and the like of the present specification will be described in detail below, the present specification is not limited to the below embodiments and the like, and optional modifications may be made within a scope that does not deviate from the spirit of the present specification. Note that in the present specification, "from A to B" or "A to B" are used as expressions that include the starting and ending numerical values or physical quantities. Furthermore, in the present specification, "at least one of A and B" means "one or both of A and B." That is, "at least one of A and B" includes "A only," "B only," and "both A and B." Unless otherwise indicated, "ppm" and "%" indicated in the present specification refer to ppm by weight and wt. %.

1. Aquaculture Shrimps

The present specification relates to an aquaculture shrimp containing carotenoids, whose second antenna is not broken.

"Shrimps" that serve as the subject of the present specification includes, without being limited to its size, a so-called lobster, prawn, and shrimp in the classification of foods.

Shrimps that serve as the subject of the present specification are academically classified under the order of Decapoda, superfamily of Penaeoidea. In the superfamily Penaeoidea, the family Penaeidae is included. Organisms of the family Penaeidae include shrimps belonging to the genus of *Farfantepenaeus, Fenneropenaeus, Litopenaeus, Marsupenaeus, Melicertus, Metapenaeopsis, Metapenaeus, Penaeus, Trachypenaeus, Xiphopenaeus*, for example.

Among the Penaeidae, edible shrimps include kuruma shrimp (*Marsupenaeus japonicus*), minami kuruma shrimp (*Melicertus canaliculatus*), black tiger (*Penaeus monodon*), chinese white shrimp (*Penaeus chinensis*), green tiger shrimp (*Penaeus semisulcatus*), western king shrimp (*Penaeus latisulcatus*), indian shrimp (*Fenneropenaeus indicus*), sand shrimp (*Metapenaeus ensis*), middle shrimp (*Metapenaeus intermedius*), *Penaeus occidentalis*, blue shrimp (*Penaeus stylirostris*), red tail shrimp (*Penaeus penicillatus*), whiteleg shrimp (*Litopenaeus vannamei*), for example; however, they are not limited thereto.

In particular, whiteleg shrimp (*Litopenaeus vannamei*) that belongs to the genus *Litopenaeus* in the family Penaeidae is one of the subjects in the present specification.

Shrimps include nektonic species and non-nektonic species. As nektonic species can be used in a water tank in three dimensions, they are suitable in production at an overcrowded state. Either species may be used in the present specification; however, at an overcrowded state, contact frequency increases and the possibility of having a defect in the second antenna is higher, and thus, the nektonic species may be used. Examples of nektonic species include sakura shrimp (*Lucensosergia lucens*), pacific pink shrimp (*Pandalus eous*), chinese white shrimp (*Penaeus chinensis*), sand shrimp (*Metapenaeus ensis*), and whiteleg shrimp (*Litopenaeus vannamei*).

"Aquaculture shrimps" refer to an aquacultured shrimp, and any shrimp aquacultured in either fresh water or sea water (including artificial sea water) is included. Shrimps contained in a system where artificial conditions are imposed are included. Such system allows the farming of this group of crustacean in a suitable embodiment, which can control the growing and harvesting of shrimps to be provided for use, processing, and/or sale.

"Carotenoids" refers to yellow to red, or purple insoluble polyene pigments that are produced by green plant and certain kinds of fungi, yeast, mushrooms, bacteria, and the like. "Carotenoids" include any molecules that are classified into yellow to red pigments such as carotenes and xanthophylls. Of these, astaxanthin, in particular, artificially synthesized artificial astaxanthin is one of the carotenoids that is the subject of the present specification. Details of synthetic astaxanthin are provided herein below. In one embodiment of the present specification, an aquaculture shrimp contains carotenoids greater than or equal to 0.1%, greater than or equal to 0.3%, greater than or equal to 0.5%, greater than or equal to 0.8%, and greater than or equal to 1%.

Figure 1:
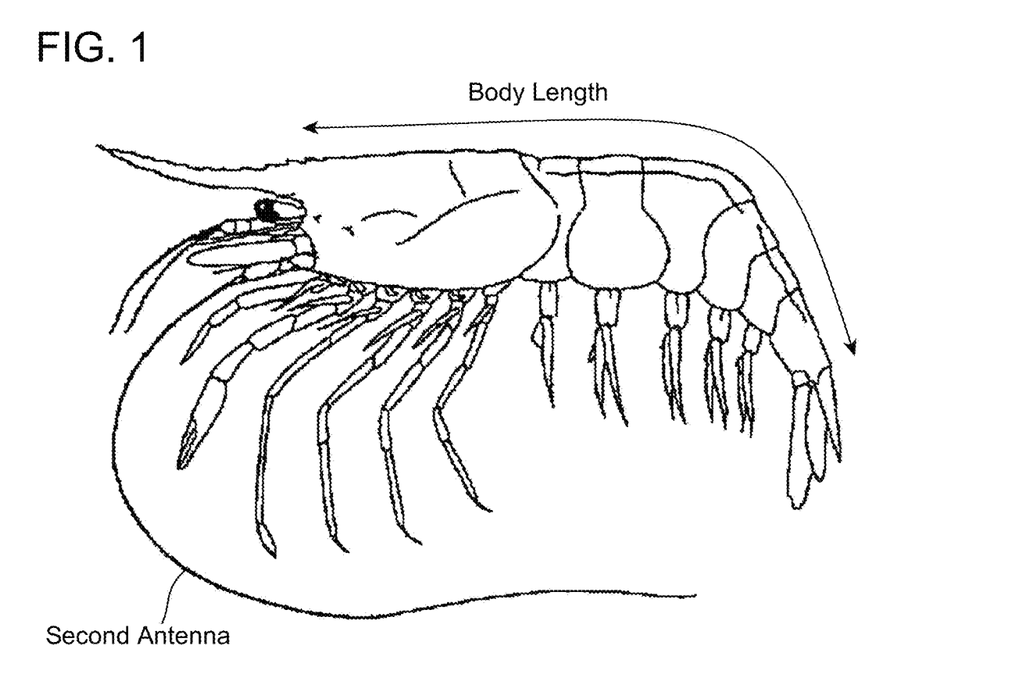
FIG. 1 is a schematic diagram of the appearance of a shrimp (Lateral view).

"Second antenna" refers to an antenna that is commonly referred to as the mustache (refer to FIG. 1). "The second antenna is not broken" refers to that the second antenna has no damage. In such case, the two antennas on the left and right are approximately of the same length. The aquaculture shrimp of the present specification includes cases where the length of the second antenna is longer than the body length. When this second antenna is defective, the product value is reduced. Moreover, when the second antenna is defective, it would affect the health condition of the shrimp. Generally, as the second antenna is longer than or equal to the body length without a damage, in the present specification, an individual having a second antenna with a length less than or equal to the body length is considered to have a damage in the second antenna. The second antenna is measured from the root of the antenna using a ruler.

The body color of the shrimp is particularly important in the market. Red color is valued highly at a boiled state, whereas white color is valued highly to be eaten raw. "Value a of body color", "value b of body color", and "colorfulness of body color" refer to value a*, value b*, and colorfulness of the first abdominal segment of the shrimp subjected for measurement, respectively. Value a*, value b*, and colorfulness of the body color can be measured at the first abdominal segment of the shrimp which is the subject of measurement by a chroma meter (for example, CR-300; Konica Minolta Inc.).

The value a* of the body color of the aquaculture shrimp of the present specification may be greater than or equal to −0.08, greater than or equal to −0.06, greater than or equal to −0.04, greater than or equal to −0.02, or greater than or equal to 0. Moreover, value b of the color may be greater than or equal to 0.4, greater than or equal to 0.35, greater than or equal to 0.3, greater than or equal to 0.25, greater than or equal to 0.2, or greater than or equal to 0.15. The colorfulness of the body color may be less than or equal to 1.8, less than or equal to 1.75, less than or equal to 1.7, less than or equal to 1.65, or less than or equal to 1.6.

The weight of the aquaculture shrimp of the present specification may be greater than or equal to 10 g, greater than or equal to 11 g, greater than or equal to 12 g, greater than or equal to 13 g, greater than or equal to 14 g, or greater than or equal to 15 g. The body length of the aquaculture shrimp of the present specification may be greater than or equal to 5 cm, greater than or equal to 6 cm, greater than or equal to 7 cm, greater than or equal to 8 cm, greater than or equal to 9 cm, greater than or equal to 10 cm, greater than or equal to 11 cm, or greater than or equal to 12 cm. Here, the "body length" refers to the length from the dent of the thorax posterior to the eye (eye socket) to the end of the tail (refer to FIG. 1).

Moreover, the present specification relates to an aquaculture shrimp having a particular body color after killing in ice with water.

In the killing in ice with water of aquaculture shrimps, the ice may be prepared from fresh water; however, sea water diluted with water to a certain degree or sea water could be used. Furthermore, artificial sea water may be used. In a container, fresh water, sea water diluted with water to a certain degree, sea water, or artificial sea water is put, and the ice is prepared in the same container. When killing the shrimps, it is done so by casting the shrimps into the container. Once the shrimps are dead, they are taken out immediately from the container and kept in the refrigerator.

The value *a of the body color of the aquaculture shrimp of the present specification, 2 days after killing in ice with water, may be greater than or equal to −1.26, greater than or equal to −1.0, greater than or equal to −0.9, greater than or equal to −0.8, greater than or equal to −0.7, or greater than or equal to −0.6. The value *b of the body color, 2 days after killing in ice with water, may be greater than or equal to −4.3, greater than or equal to −4.0, greater than or equal to −3.0, greater than or equal to −2.0, greater than or equal to −1.0, greater than or equal to 0, greater than or equal to 1.0, or greater than or equal to 2.0. The colorfulness of the body color, 2 days after killing in ice with water, may be less than or equal to 4.62, less than or equal to 4.0, less than or equal to 3.5, less than or equal to 3.0, less than or equal to 2.5, or less than or equal to 2.0.

2. Culturing Methods of Aquaculture Shrimps (Methods for Producing Aquaculture Shrimps)

Hereinbelow, culturing methods of aquaculture shrimps (methods for producing aquaculture shrimps) of the present specification are explained. The culturing method of the present specification is a method of culturing aquaculture shrimps of the present specification as stated above.

According to the culturing method of the present specification, in one embodiment, a shrimp which has a good appearance with respect to color and the length of the second antenna can be produced. In another embodiment, a shrimp could be produced so that the occurrence of a shrimp with a deformed body shape is suppressed. In another embodiment, the probability of the shrimp dying in the course of culturing is reduced, thus the yield is increased, and the shrimp could be raised to a predetermined size.

In the culturing method of the present specification, the nursery is not particularly limited, and it is appropriately selected in consideration to the kind, size, and the like, of the target shrimp. The culturing method of the present specification is carried out by culturing in sea, river, lakes and the like. Land-farming generally allows the shrimps to grow at an overcrowded state, resulting in a large number of damage in the second antenna of the aquaculture shrimps. For this reason, in one embodiment, land-farming is effective.

The kinds of shrimp subjected for culturing are as mentioned above. The shrimps subjected for the culturing method of the present specification is not particularly limited, and include baby shrimps and parent shrimps.

The "baby shrimp" referred in the present specification refers to those that are less than 1 g of body weight, and those that are growing from egg to baby shrimp are not included.

Moreover, "parent shrimp" refers to a grown up of the baby shrimp described above. The parent shrimp, in case of whiteleg shrimp, for example, in general, is raised up to approximately greater than or equal to 15 g and then shipped.

In the culturing method of the present specification, feed containing carotenoids are given to the shrimps. Such given carotenoids are allowed to accumulate in the shrimps. The source of carotenoids is not particularly limited. Carotenoids include astaxanthin, in particular, synthetic astaxanthin. Synthetic astaxanthin includes astaxanthin produced by chemical synthesis. Synthetic astaxanthin includes a large number of isomers of 3S, 3S' form, 3S, 3R' form (meso-form), 3R, 3R' form, further includes cis-, trans-forms of conjugated double bond at the center of the molecule, for example, all cis-, 9-cis form and 13-cis form, and thus, it can be easily distinguished from natural astaxanthin. Apart from astaxanthin, carotenoids may include lutein and lycopene, for example.

A suitable feed is a feed containing greater than or equal to 50 ppm, greater than or equal to 60 ppm, greater than or equal to 70 ppm, greater than or equal to 80 ppm, greater than or equal to 90 ppm, or greater than or equal to 100 ppm of astaxanthin (particularly synthetic astaxanthin). The method of containing astaxanthin in the feed may be performed by dissolving in oil, spraying by spray, adding and mixing, or a combination thereof, or astaxanthin may be added as one of the ingredients when the feed itself is prepared. Regarding the feeding amount of the astaxanthin-containing feed of a predetermined concentration given to shrimps subjected for culturing, greater than or equal to 1%, greater than or equal to 2%, greater than or equal to 3%, greater than or equal to 4%, greater than equal to 5%, greater than or equal to 6%, greater than or equal to 7%, greater than or equal to 8%, greater than or equal to 9%, or greater than equal to 10% of the feed may be fed to satiation. In a day, the feed may be given once, twice, three times, four times, or five times. The feeding may be carried out continuously while monitoring residual feed. The period of the shrimp subjected for culturing given with feed containing astaxanthin of a predetermined concentration is, for example, longer than or equal to 7 days, longer than or equal to 14 days, longer than or equal to 28 days, longer than or equal to 35 days, longer than equal to 42 days, longer than equal to 49 days, longer than or equal to 56 days, longer than equal to 63 days, longer than or equal to 70 days, longer than or equal to 77 days, longer than or equal to 84 days, or longer than or equal to 90 days. When shrimp is cultured overcrowdedly by land-farming in this way, damages caused in many of the second antennas is usually inevitable. Though the farming with feed containing a large quantity of carotenoid such as astaxanthin results in the production of shrimps with good appearance at a state where the second antenna is relatively well-preserved. In addition, less damage in the shrimp's second antenna imposes less stress to the shrimps and they can be farmed at a healthy state.

The water quality is regularly checked and adjusted so to be within the appropriate range. The shrimps are farmed at a pH of 5 to 10, 6 to 9, or 7 to 8. When pH drops or rises, the pH is adjusted by adding an alkali agent or an acid or adjusting the water exchange rate. The farming is carried out while maintaining the water temperature at 23 to 32° C., 25 to 30° C., or 27 to 29° C. The water temperature can be adjusted by heating with solar light, heater, and the like, or by cooling with a cooler box, ice, and the like.

3. Applied Products Including Aquaculture Shrimp or the Processed Products Thereof The aquaculture shrimp according to the present specification may be used as is or may be further processed by extraction, grinding, and the like. Also, a composition containing aquaculture shrimp may be produced by combining an aquaculture shrimp or a processed product thereof and optional components. The formulation ratio of the optional components could be appropriately selected and determined depending on the purpose.

As in case of land-farming, in particular, where production control can be strictly performed, the shrimps can be offered to the market to be eaten raw. Such use is no restricted; however, specific examples include food, feed, medicine, and the like.

The food which serves as the subject of the aquaculture shrimp and the processed product thereof of the present specification is not particularly limited, and it can be used as is or mixed with various kinds of food. For example, food includes foodstuffs such as sausage, ham, processed fish products. In addition, the aquaculture shrimp and the processed product thereof of the present specification can also be used as a feed for farming and aquaculturing.

In addition, the aquaculture shrimp and the processed product thereof of the present specification can also be used as ingredients of pharmaceutical agents, quasi drugs, and functional foods. "Functional food" as used herein refers to foods and/or beverages to be ingested for maintaining health, in addition to general foods, and this term includes Food for specified health uses and Food with nutrient function claims (health functional food), health food, nutritional supplements, nutrition health food, and the like.

In the case of commercializing as pharmaceutical agents, quasi-drugs, functional food, various additives recognized for each item, specifically, coloring agents, preservatives, thickening stabilizers, antioxidants, bleaching agents, antibacterial and antifungal agents, acidulants, seasonings, emulsifiers, enhancers, manufacturing agents, fragrance, and the like, may be added.

EXAMPLES

The present specification is described specifically below by citing examples, but the present invention is not limited to these examples.

Example 1 Preparation of Feed

Astaxanthin was purchased from DSM Nutrition Japan KK. The product with a product name CAROPHYLL Pink was purchased and used. This product was produced by chemical synthesis. For the basic feed, the composition of Table 1 was formulated for a pellet mill with a 3-path conditioner. The pellet size was manufactured at 2.4 mm.

The basic feed was measured and 2.5 ppm of astaxanthin was contained. This is believed to be because fish oil contains astaxanthin.

Experimental feed containing astaxanthin was prepared so that the basic feed was supplemented with 50 ppm of astaxanthin and 100 ppm of astaxanthin. Astaxanthin was dissolved in fish oil, placed in a plastic bag together with the basic feed, and this was mixed well. Feed was stored at 4° C. for 3 days or longer and then used.

TABLE 1

| Contents | % |
|---|---|
| Whole wheat flour | 36.8 |
| Soybean meal (47%) | 26 |
| Squid meal (72%) | 6 |
| Fish meal (62%) | 15 |
| Calcium phosphate | 4.5 |
| Soybean lecithin | 2 |
| Cholesterol | 0.12 |
| Potassium chloride | 2.5 |
| Calcium carbonate | 1 |
| Magnesium oxide | 1.6 |
| Minerals/Vitamin premix | 0.44 |
| Vitamin C | 0.04 |
| Fish oil | 2 |
| Soybean Oil | 2 |
| Total Percentage | 100 |

Feed were prepared so that 50 ppm of astaxanthin was added to basic feed (50 ppm astaxanthin feed) and 100 ppm of astaxanthin was added to basic feed (100 ppm astaxanthin feed). Each feed was immersed in water for 6 hours and it was confirmed that the astaxanthin amount was maintained at about 50 ppm and 100 ppm in each feed. Shrimps with an average individual weight of about 14 g were prepared and fed each feed, and 16 individuals in each experimental plot were kept for 15 days.

The average values of the value L, value a, and value b of 16 individuals in each experimental plot were taken as the values of each condition. Measurements were taken in the morning on the 1st day, 2nd day, 3rd day, 6th day, 8th day, 9th day, 12th day, and 15th day of farming. The results are shown in Table 2. In Table 2, experimental plots given with 50 ppm astaxanthin feed and 100 ppm astaxanthin feed are disclosed as "experimental plot of 50 ppm" and "experimental plot of 100 ppm", respectively.

Figure 2:
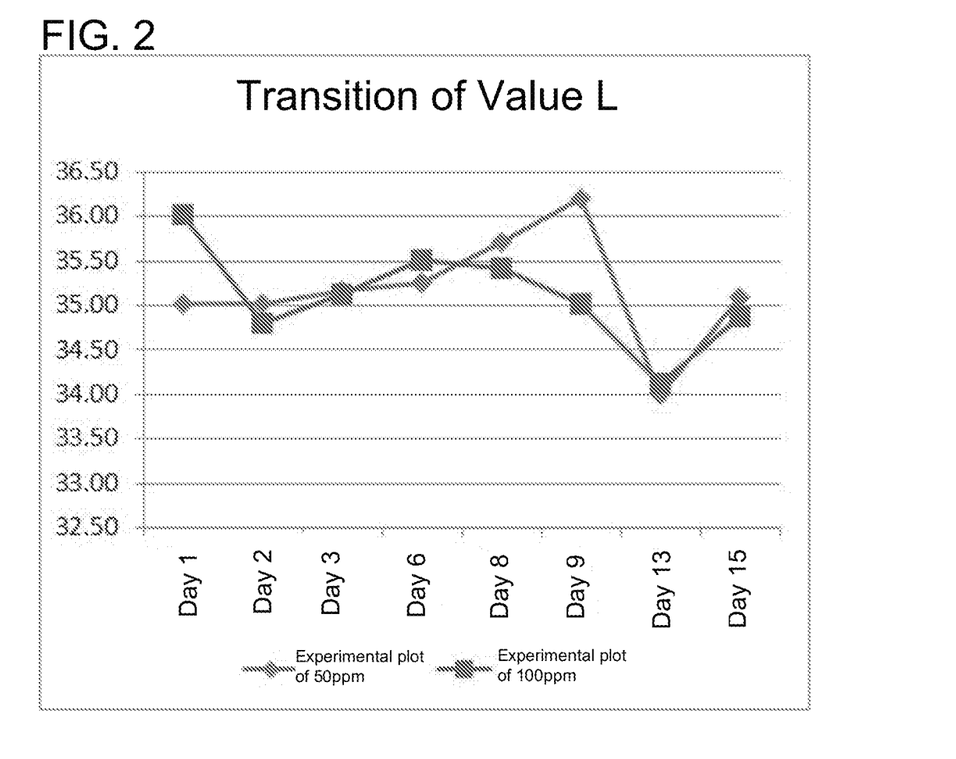
FIG. 2 is a graph showing the transition of value L of the shrimps in an experimental plot of 50 ppm and an experimental plot of 100 ppm.
Figure 3:
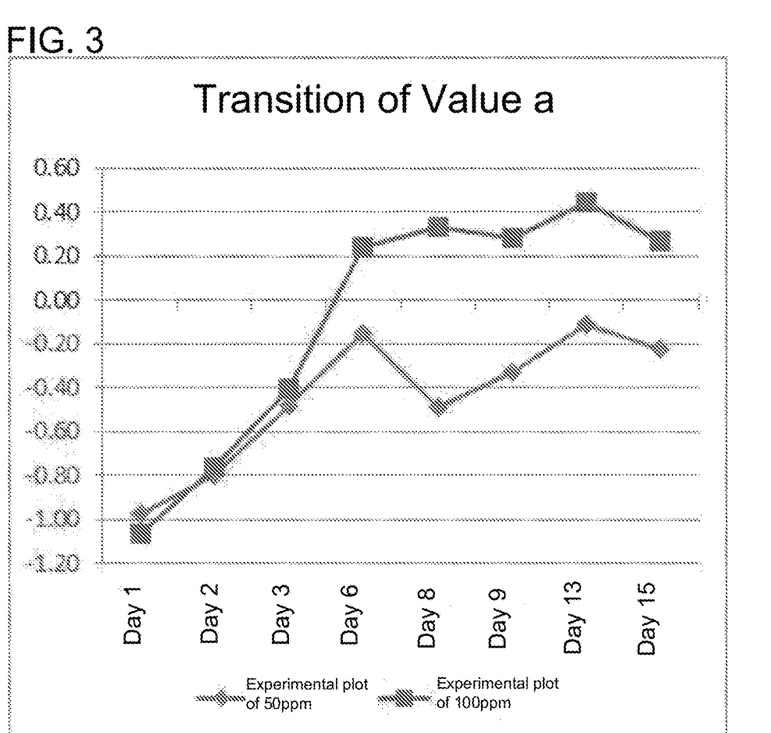
FIG. 3 is a graph showing the transition of value a of the shrimps in an experimental plot of 50 ppm and an experimental plot of 100 ppm.
Figure 4:
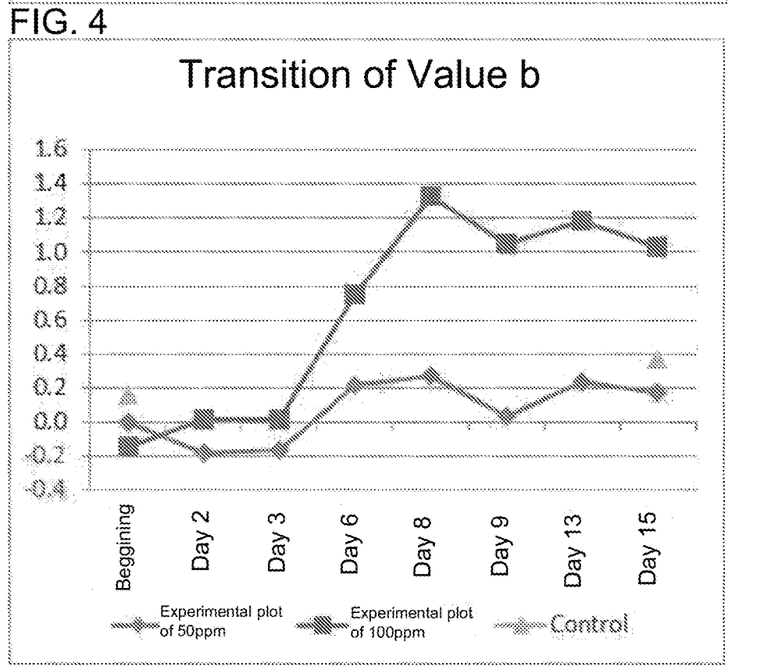
FIG. 4 is a graph showing the transition of value b of the shrimps in an experimental plot of 50 ppm and an experimental plot of 100 ppm.
Figure 5:
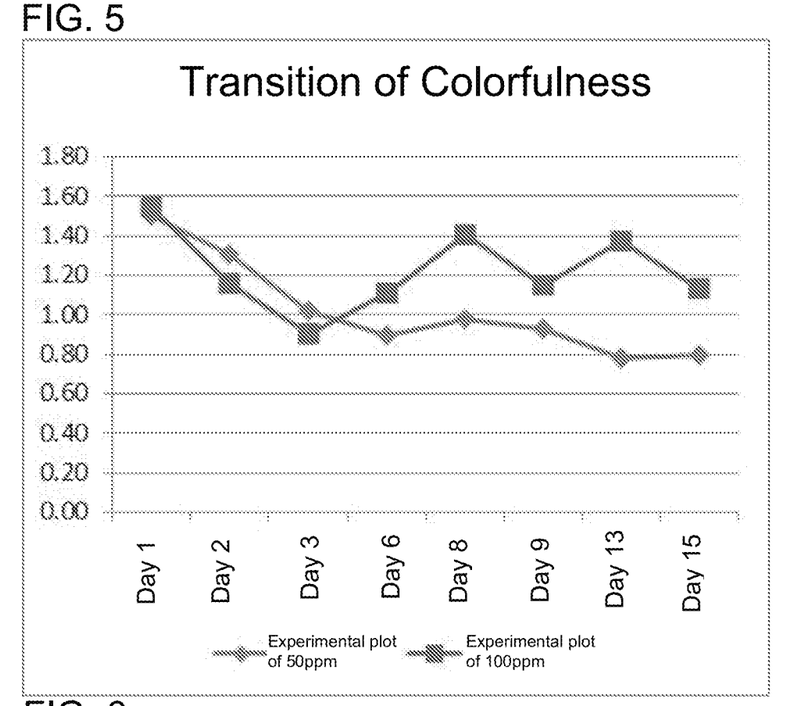
FIG. 5 is a graph showing the transition of colorfulness of the shrimps in an experimental plot of 50 ppm and an experimental plot of 100 ppm.

In FIG. 2, FIG. 3, FIG. 4. and FIG. 5, the transition of each of value L, value a, value b, and colorfulness in experimental plots of 50 ppm and 100 ppm is provided. When astaxanthin-enriched feed is given, a tendency of increasing value L, value a, and value b was confirmed.

TABLE 2

| | | Number of days of farming (Days) | | | | | | | |
|---|---|---|---|---|---|---|---|---|---|
| | | 1 | 2 | 3 | 6 | 8 | 9 | 13 | 15 |
| Experimental plot of 50 ppm | Value L | 35.03 | 35.01 | 35.16 | 35.26 | 35.71 | 36.22 | 34 | 35.09 |
| | Value a | −0.98 | −0.8 | −0.48 | −0.15 | −0.49 | −0.33 | −0.11 | −0.22 |
| | Value b | 0 | −0.18 | −0.17 | 0.22 | 0.27 | 0.04 | 0.23 | 0.17 |
| | Colorfulness | 1.51 | 1.31 | 1.02 | 0.89 | 0.97 | 0.92 | 0.78 | 0.79 |
| Experimental plot of 100 ppm | Value L | 36.03 | 34.79 | 35.13 | 35.52 | 35.42 | 35.01 | 34.12 | 34.87 |
| | Value a | −1.07 | −0.76 | −0.4 | 0.24 | 0.33 | 0.29 | 0.44 | 0.27 |
| | Value b | −0.15 | 0.02 | 0.02 | 0.75 | 1.33 | 1.05 | 1.19 | 1.03 |
| | Colorfulness | 1.55 | 1.16 | 0.90 | 1.11 | 1.40 | 1.15 | 1.37 | 1.14 |

Example 2 Methods for Farming Shrimps

Whiteleg shrimp (*Litopenaeus vannamei*) having an average individual weight of 14 g was subjected for farming. For farming, 80 L of water was placed in a 100 L cylinder water tank and used. Flowing water was managed by setting the water exchange rate to 8 to 10 times/day. The water tank was installed indoor, the light from the side and bottom was shielded, and the lights were lit from around 8 AM to 5 PM. Ventilation was carried out by placing the air stone in the central part. Water temperature was set at 28° C. and DO (Dissolved Oxygen) was maintained at greater than or equal to 6.1 mg/L. Feed was given every day. pH measurement was carried out once every morning.

Example 3 Measurement of Shrimp Color

The measurement of the body color of the shrimp was carried out using chroma meter CR-300 (Konica Minolta Inc.). The color was assessed by numerical values of L*a*b* color system. The site to be measured by the chroma meter was determined to be the first abdominal segment, and the two points on the left side and the right side of the body of each sample were measured, and the average value was used.

Example 4 Growth and Mortality Rates

Three experimental plots were set for basic feed, 50 ppm astaxanthin feed, and 100 ppm astaxanthin feed, and the shrimps were farmed using each feed for 90 days. Sixteen individuals of the shrimps were used for each plot. Individual body weight was measured at the beginning of the experiment, 30th day, 50th day, 70th day, and 90th day, and the average was calculated. The results are shown in Table 4.

Mortality rate after 90 days is shown in Table 5. Survival rate was calculated without including the sample individuals. All natural death was caused by the molted individuals being cannibalized. In Tables 3 and 4, experimental plots given with 50 ppm astaxanthin feed and 100 ppm astaxanthin feed are described as "experimental plot of 50 ppm" and "experimental plot of 100 ppm", respectively. The experimental plot given with astaxanthin-enriched feed resulted in a good growth and a high survival rate.

TABLE 3

| | Weight of shrimps (g) | | |
| --- | --- | --- | --- |
| | Experimental plot of 50 ppm | Experimental plot of 100 ppm | Experimental plot of basic feed |
| Starting point | 14.08 | 14.69 | 13.89 |
| 30th day | 15.69 | 14.42 | 16.43 |
| 50th day | 16.99 | 19.35 | — |
| 70th day | 17.58 | 21.06 | 17.13 |
| 90th day | 18.66 | 22.11 | 17.44 |
| Amount of increase | 4.58 | 7.42 | 3.55 |

TABLE 4

| | Mortality rate | | | Number of individuals when starting the experiment | Number of individuals when ending the experiment | Survival rate (%) |
| --- | --- | --- | --- | --- | --- | --- |
| | Total number | Natural death | Sampling | | | |
| Experimental plot of 50 ppm | 2 | 1 | 1 | 16 | 14 | 93.3 |
| Experimental plot of 100 ppm | 4 | 3 | 1 | 16 | 12 | 80 |
| Experimental plot of basic feed | 9 | 8 | 1 | 16 | 7 | 46.7 |

Example 5 Measurement of the Second Antenna

Three experimental plots were set for basic feed, 50 ppm astaxanthin feed, and 100 ppm astaxanthin feed, and the shrimps were farmed using each feed for 90 days. Sixteen individuals of the shrimps with an average individual weight of about 14 g when starting were used for each plot. The length of the second antenna was observed on the 19th day, 27th day, 34th day, 40th day, 47th day, 52nd day, 55th day, 59th day, 65th day, 73rd day, 85th day, and 90th day. L refers to the second antenna longer than the body length, S refers to those less than or equal to 2 cm, and M refers to those that are between L and S.

Figure 6:
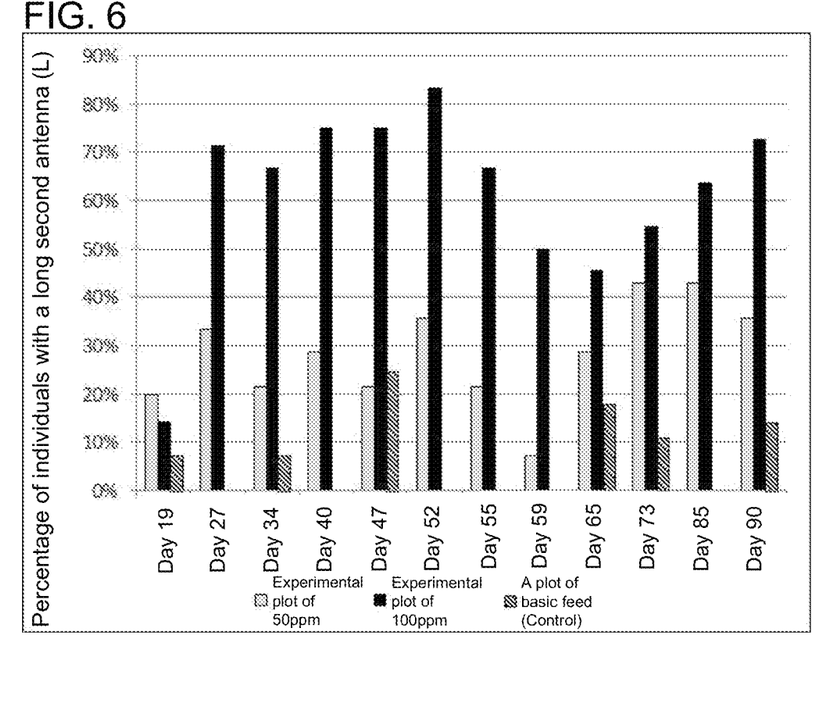
FIG. 6 is a graph showing the percentage of individuals with a long second antenna (L) in an experimental plot of 50 ppm, an experimental plot of 100 ppm, and a plot of basic feed (Control).
Figure 7:
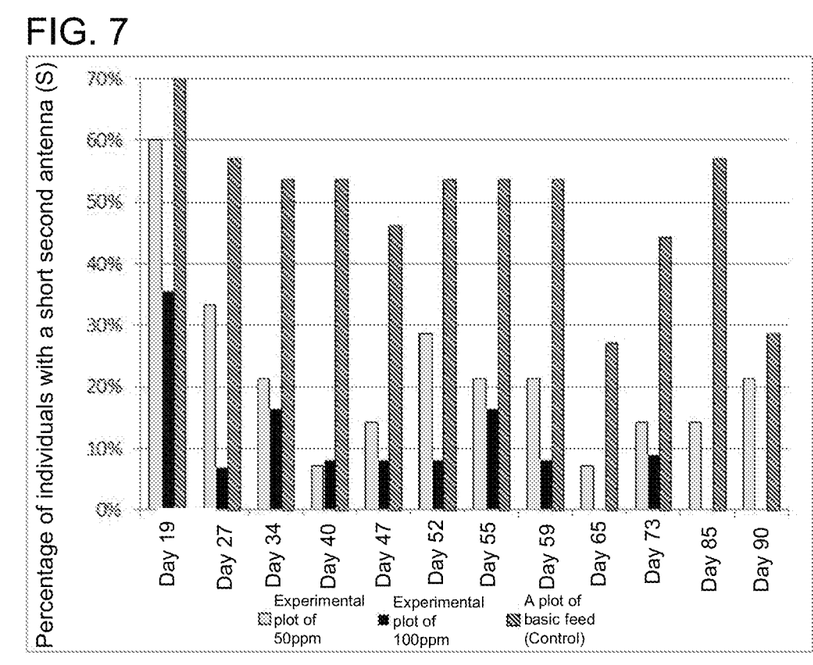
FIG. 7 is a graph showing the percentage of individuals with a short second antenna (S) in an experimental plot of 50 ppm, an experimental plot of 100 ppm, and a plot of basic feed (Control).

The results are shown in Table 5. The percentage of individuals with a long second antenna (L) and a short second antenna (S) in an experimental plot of 50 ppm, an experimental plot of 100 ppm, and a plot of basic feed (Control) are shown in FIG. 6 and FIG. 7. It was confirmed that astaxanthin-enriched plots had many shrimps with a long second antenna.

TABLE 5

| | Length of the second antenna | Number of individuals | | | | | |
| --- | --- | --- | --- | --- | --- | --- | --- |
| | | 19th day | 27th day | 34th day | 40th day | 47th day | 52nd day |
| Experimental plot of basic feed | L | 0 | 0 | 1 | 0 | 3 | 2 |
| | M | 3 | 6 | 5 | 6 | 3 | 3 |
| | S | 12 | 8 | 7 | 7 | 6 | 7 |
| Experimental plot of 50 ppm | L | 3 | 5 | 3 | 4 | 3 | 5 |
| | M | 3 | 5 | 8 | 9 | 9 | 5 |
| | S | 9 | 5 | 3 | 1 | 2 | 4 |
| Experimental plot of 100 ppm | L | 2 | 10 | 8 | 9 | 9 | 10 |
| | M | 7 | 3 | 2 | 2 | 2 | 1 |
| | S | 5 | 1 | 2 | 1 | 1 | 1 |
| | Length of the second antenna | Number of individuals | | | | | |
| | | 55th day | 59th day | 65th day | 73rd day | 85th day | 90th day |
| Experimental plot of basic feed | L | 1 | 2 | 2 | 1 | 0 | 1 |
| | M | 4 | 3 | 6 | 4 | 3 | 4 |
| | S | 7 | 7 | 3 | 4 | 4 | 2 |
| Experimental plot of 50 ppm | L | 3 | 1 | 4 | 6 | 6 | 5 |
| | M | 8 | 10 | 9 | 6 | 6 | 6 |
| | S | 3 | 3 | 1 | 2 | 2 | 3 |

TABLE 5-continued

| | | | | | | | |
|---|---|---|---|---|---|---|---|
| Experimental plot of 100 ppm | L | 8 | 6 | 5 | 6 | 7 | 8 |
| | M | 2 | 5 | 6 | 4 | 4 | 3 |
| | S | 2 | 1 | 0 | 1 | 0 | 0 |

L: Longer than body length,
M: Between L and S,
S: Less than or equal to 2 cm

Example 6 Change of Color after Killing in Ice with Water

Two experimental plots were set for 50 ppm astaxanthin feed and 100 ppm astaxanthin feed, and the shrimps were farmed using each feed for 90 days. The shrimps were ice killed by casting them into a container containing sea water and ice. Seven individuals from the experimental plot of 50 ppm and 5 individuals from the experimental plot of 100 ppm were sampled, ice killed, and the body color of the shrimps were measured using the chroma meter. The measurement was carried out using chroma meter CR-300 (Konica Minolta Inc.) and the color was assessed based on the numerical values of the L*a*b* color system. The site to be measured by the chroma meter was determined to be the first abdominal segment, and the two points on the left side and the right side of the body of each sample were measured, and the average value was used. The body color of the shrimps immediately after killing in ice with water and those that were preserved in the refrigerator for two days after killing in ice with water were measured using the chroma meter. The results are shown in Table 6. In experimental plots without enriched astaxanthin, value b tended to increase as time passed after killing in ice with water; however, it was confirmed that the value was suppressed in astaxanthin-enriched plots.

TABLE 6

| | Killing in ice with water | L | a | b | Colorfulness |
|---|---|---|---|---|---|
| Experimental plot of basic feed | Immediately after | 40.98 | −1.55 | −3.15 | 3.72 |
| | 2 days later | 45.53 | −1.27 | −4.4 | 4.63 |
| Experimental plot of 50 ppm | Immediately after | 38.36 | −0.17 | 1.96 | 2.06 |
| | 2 days later | 44.94 | −0.59 | 1.95 | 2.06 |
| Experimental plot of 100 ppm | Immediately after | 36.96 | −0.54 | 1.62 | 1.75 |
| | 2 days later | 45.29 | −0.76 | 1.59 | 1.9 |

The present application addresses the following.

Commercial value of shrimps can be affected by appearance in addition to freshness and taste, and the better the appearance, the higher the quality would be assessed. As the culturing of shrimps is generally carried out in an overcrowded state, each individual comes close to each other. Due to this, the antenna part which plays an important role in the appearance of shrimps is likely to be defective, and this is one of the factors which reduce the commercial value of the shrimps. Moreover, in the techniques disclosed in the above-mentioned Patent Documents 1 and 2, an improvement in the color of the aquaculture shrimp is apparently recognized; however, other aspects of appearance (such as forms) apart from color in the aquaculture shrimp have not been improved, and there has been room left for improving the color as well. Furthermore, in general, shrimps are ice killed and then distributed to the market; however, there has been room left for improving the color after the shrimps has been ice killed.

Under such circumstances, the present specification aims to provide aquaculture shrimps with good appearance.

The present specification relates to the following.

(1) An aquaculture shrimp including a carotenoid, whose second antenna is not broken.

(2) The aquaculture shrimp according to (1) produced by land farming.

(3) The aquaculture shrimp according to (1) or (2), wherein the value a of the body color is greater than or equal to −0.08.

(4) The aquaculture shrimp according to any one of (1) to (3), wherein the value b of the body color is greater than or equal to 0.15.

(5) The aquaculture shrimp according to any one of (1) to (4), wherein the colorfulness of the body color is less than or equal to 1.8.

(6) The aquaculture shrimp according to any one of (1) to (5), wherein the body weight is greater than or equal to 10 g.

(7) The aquaculture shrimp according to any one of (1) to (6), wherein the body length is greater than or equal to 5 cm.

(8) The aquaculture shrimp according to any one of (1) to (7), wherein the carotenoid is a synthetic astaxanthin.

(9) The aquaculture shrimp according to any one of (1) to (8), wherein the aquaculture shrimp is of the order Decapoda.

(10) The aquaculture shrimp according to (9), wherein the shrimp is classified in the superfamily Penaeoidea of order Decapoda.

(11) The aquaculture shrimp according to (10), wherein the shrimp is classified in the family Penaeidae of order Decapoda.

(12) The aquaculture shrimp according to (11), wherein the shrimp is classified in the genus *Litopenaeus* of the superfamily Penaeoidea.

(13) The aquaculture shrimp according to (12), wherein the shrimp is classified in *Litopenaeus vannamei* of genus *Litopenaeus*.

(14) The aquaculture shrimp according to any one of (1) to (13) which is reared by giving feed containing greater than or equal to 50 ppm of astaxanthin.

(15) The rearing method of aquaculture shrimp according to any one of (1) to (14).

(16) The method for producing aquaculture shrimp according to any one of (1) to (14) produced by land-farming.

(17) A food, feed, and medicine including the aquaculture shrimp or the processed product thereof according to any one of (1) to (14).

(18) An aquaculture shrimp, wherein the value a of the body color 2 days after killing in ice with water is greater than or equal to −1.26.

(19) The aquaculture shrimp according to (18), wherein the value b of the body color is greater than or equal to −4.3.

(20) The aquaculture shrimp according to (18) or (19), wherein the colorfulness of the body color is less than or equal to 4.62.

(21) A rearing method of an aquaculture shrimp which is a production method carried out by land-farming, the method including giving feed containing greater than or equal to 50 ppm of astaxanthin.

(22) The rearing method of aquaculture shrimp according to (21), wherein the rearing is carried out at a water temperature set to 23 to 32° C.

(23) The rearing method of aquaculture shrimp according to (21) or (22), wherein the rearing is carried out by maintaining DO greater than or equal to 6.1 mg/L.

(24) The rearing method of aquaculture shrimp according to any one of (21) to (23), wherein the rearing is carried out in a light-dark cycle.

According to the present specification, an aquaculture shrimp with good appearance is provided.

INDUSTRIAL APPLICABILITY

Aquaculture shrimps or processed product of the same of the present specification could be used as ingredients in various applied products including food, feed, pharmaceutical agents, and thus, they are industrially beneficial.

Obviously, numerous modifications and variations of the present invention are possible in light of the above teachings. It is therefore to be understood that within the scope of the appended claims, the invention may be practiced otherwise than as specifically described herein.

What is claimed is:

1. An aquaculture shrimp produced by a method of farming aquaculture shrimps, comprising:
   keeping shrimps in a land-farming nursery; and
   feeding to the shrimps kept in the land-farming nursery a feed comprising a carotenoid in an amount of 50 ppm or greater,
   wherein the keeping includes monitoring a ratio of shrimps having pairs of second antennas that are not broken and are longer than respective body lengths of the shrimps in the land-farming nursery such that the ratio is at least 50%.

2. The aquaculture shrimp according to claim 1, wherein the keeping includes selecting the shrimps having the pair of second antennas that are longer than the body lengths, respectively.

3. The aquaculture shrimp according to claim 1, wherein the keeping includes monitoring for the shrimps having value a of body color that is greater than or equal to −0.08.

4. The aquaculture shrimp according to claim 1, wherein the keeping includes monitoring for the shrimps having value b of body color that is greater than or equal to 0.15.

5. The aquaculture shrimp according to claim 1, wherein the keeping includes monitoring for the shrimps having colorfulness of body color that is less than or equal to 1.8.

6. The aquaculture shrimp according to claim 1, wherein the keeping includes monitoring for the shrimps having body weights that are greater than or equal to 10 g.

7. The aquaculture shrimp according to claim 1, wherein the keeping includes monitoring for the shrimps having body lengths that are greater than or equal to 5 cm.

8. The aquaculture shrimp according to claim 1, wherein the carotenoid comprises synthetic astaxanthin.

9. The aquaculture shrimp according to claim 1, wherein the shrimps are of order Decapoda.

10. The aquaculture shrimp according to claim 9, wherein the shrimps are classified in superfamily Penaeoidea of order Decapoda.

11. The aquaculture shrimp according to claim 10, wherein the aquaculture shrimp is classified in family Penaeidae of superfamily Penaeoidea.

12. The aquaculture shrimp according to claim 11, wherein the shrimps are classified in genus *Litopenaeus* of superfamily Penaeoidea.

13. The aquaculture shrimp according to claim 12, wherein the shrimps are classified in *Litopenaeus vannamei* of genus *Litopenaeus*.

14. The aquaculture shrimp according to claim 1, wherein the carotenoid in the feed is astaxanthin, and the amount of astaxanthin is greater than or equal to 100 ppm.

15. A composition, comprising:
    the aquaculture shrimp of claim 1 or a processed product thereof.

16. A method of farming aquaculture shrimps, comprising:
    keeping shrimps in a land-farming nursery; and
    feeding to the shrimps kept in the land-farming nursery a feed comprising carotenoid in an amount of 50 ppm or greater,
    wherein the keeping includes monitoring a ratio of shrimps having pairs of second antennas that are not broken and are longer than respective body lengths of the shrimps in the land-fanning nursery such that the ratio is at least 50%.

17. The method of claim 16, wherein the carotenoid in the feed is astaxanthin.

18. The method of claim 16, further comprising:
    killing the shrimps in ice with water; and
    selecting shrimps having value a of body color 2 days after the killing in ice with water that is greater than or equal to −1.26.

19. The method of claim 18, wherein the selecting includes selecting the shrimps having value b of body color that is greater than or equal to −4.3.

20. The method of claim 18, wherein the selecting includes selecting the shrimps having colorfulness of body color that is less than or equal to 4.62.

21. The method of claim 16, wherein the carotenoid in the feed is astaxanthin, and the amount of astaxanthin is greater than or equal to 100 ppm.

22. The method of claim 16, wherein the shrimps are kept in the land-farming nursery at a water temperature set to 23 to 32° C.

23. The method of claim 16, wherein the shrimps in the land-farming nursery includes maintaining DO greater than or equal to 6.1 mg/L.

24. The method of claim 16, wherein the shrimps in the land-farming nursery are kept in a light-dark cycle.

* * * * *